(12) United States Patent
LaMonica

(10) Patent No.: US 8,100,846 B1
(45) Date of Patent: Jan. 24, 2012

(54) SPINAL TRACTION AND RESTORATION USING POINTABLE CONSTRAINED INFLATOR

(76) Inventor: John J. LaMonica, White Plains, NY (US)

( * ) Notice: Subject to any disclaimer, the term of this patent is extended or adjusted under 35 U.S.C. 154(b) by 459 days.

(21) Appl. No.: 12/288,073

(22) Filed: Oct. 15, 2008

Related U.S. Application Data

(60) Provisional application No. 60/999,077, filed on Oct. 15, 2007.

(51) Int. Cl.
*A61F 5/00* (2006.01)
*A61H 1/00* (2006.01)
*A47C 16/00* (2006.01)

(52) U.S. Cl. ............... 602/32; 602/13; 602/18; 602/19; 606/240; 128/845; 601/39; 601/84; 5/636; 5/655.3

(58) Field of Classification Search ............ 602/13, 602/18, 19, 32, 36, 38–40; 606/240; 128/845; 601/39, 50–55, 84–86, 88–92, 96–100, 105, 601/112–116, 134; 5/636–638, 644, 648, 5/653, 654, 655.3
See application file for complete search history.

(56) References Cited

U.S. PATENT DOCUMENTS

| | | |
|---|---|---|
| 3,596,655 A | 8/1971 | Corcoran |
| 4,805,603 A | 2/1989 | Cumberland |
| 5,147,287 A | 9/1992 | Jewell et al. |
| 5,382,226 A | 1/1995 | Graham |
| 5,403,266 A | 4/1995 | Bragg et al. |
| 5,441,479 A | 8/1995 | Chitwood |
| 5,454,781 A | 10/1995 | Chitwood |
| 5,569,176 A | 10/1996 | Graham |
| 5,626,616 A | 5/1997 | Speece |
| 5,662,597 A | 9/1997 | Chitwood |
| 5,709,649 A | 1/1998 | Chitwood |
| 5,713,841 A * | 2/1998 | Graham ...................... 602/32 |
| 5,906,586 A | 5/1999 | Graham |
| 5,916,185 A | 6/1999 | Chitwood |
| 6,110,194 A | 8/2000 | Saber |
| 6,506,174 B1 | 1/2003 | Saunders et al. |
| 6,652,564 B1 | 11/2003 | Harris et al. |
| 6,681,770 B1 | 1/2004 | Dreher |
| 6,899,690 B2 | 5/2005 | Saunders et al. |
| 6,945,986 B2 | 9/2005 | Lope |
| 6,971,997 B1 | 12/2005 | Ryan et al. |
| 7,060,085 B2 | 6/2006 | Graham et al. |
| 7,108,671 B2 | 9/2006 | Saunders et al. |
| 2003/0212352 A1* | 11/2003 | Kahn ........................ 601/98 |
| 2007/0233190 A1* | 10/2007 | Forsey et al. ............. 606/237 |

* cited by examiner

*Primary Examiner* — Patricia Bianco
*Assistant Examiner* — Keri J Nelson
(74) *Attorney, Agent, or Firm* — McCormick, Paulding & Huber LLP

(57) ABSTRACT

Spinal traction and restoration using application of forces in user-selectable distinct unitary directions by a rotatable pointable constrained inflator proximate a device base. The constrained inflator provides selectable, variable and pointable force to effect any of the following therapies: [1] Axial Traction; [2] Force to Upper Cervical Spine; [3] Force to Mid-Cervical Spine; [4] Force to Lower Cervical Spine; and [5] Traction Force Applied to Upper Thoracic Spine.

11 Claims, 17 Drawing Sheets

-- Prior Art --

-- Prior Art --

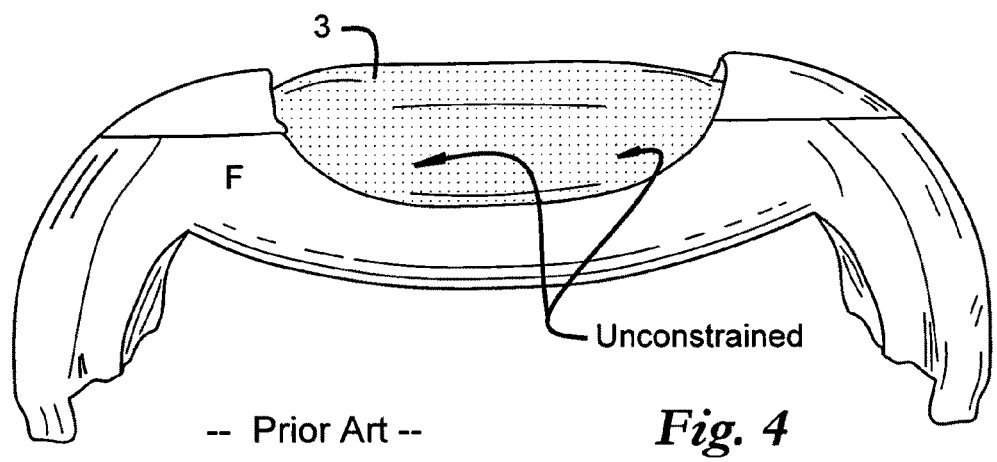
-- Prior Art --  *Fig. 4*
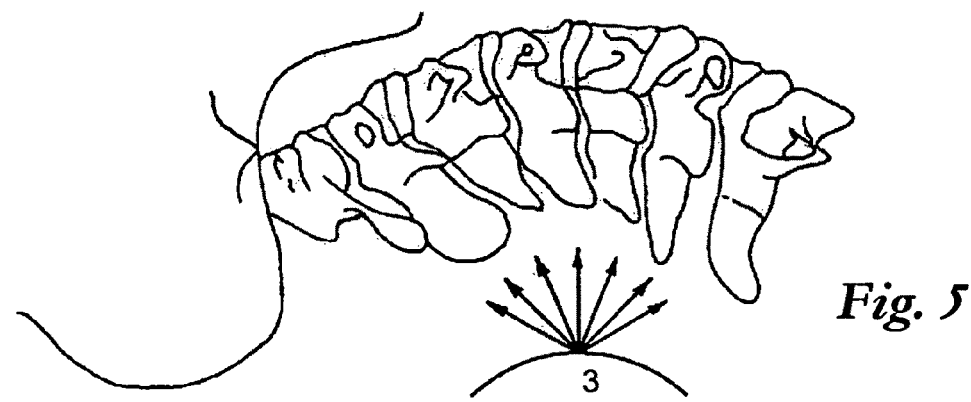
*Fig. 5*
-- Prior Art --
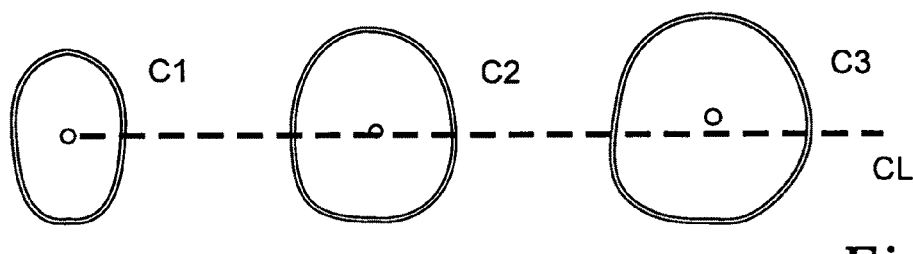
*Fig. 6*
-- Prior Art --

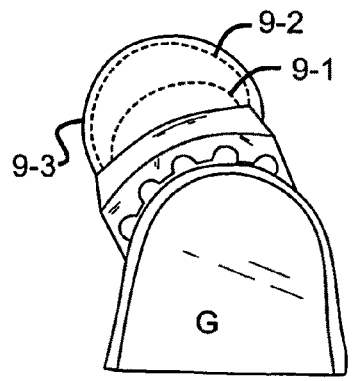
*Fig. 15*
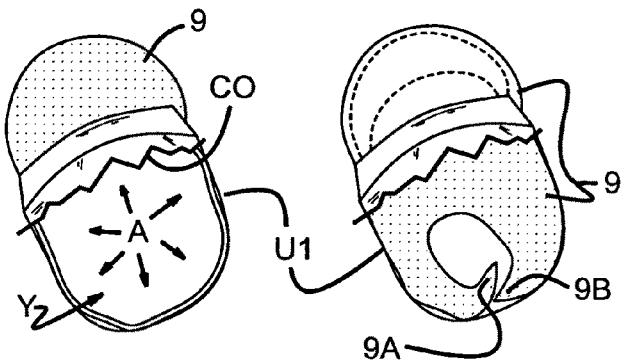
*Fig. 16*   *Fig. 17*
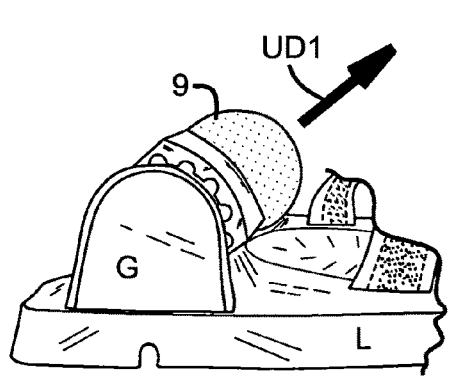
*Fig. 18*
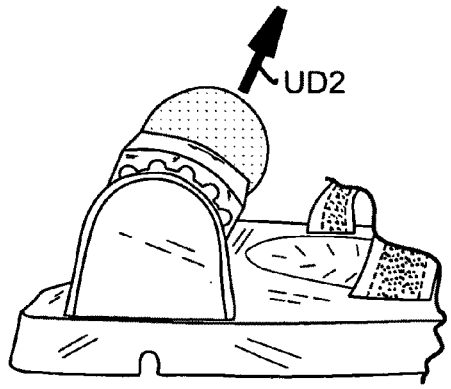
*Fig. 19*
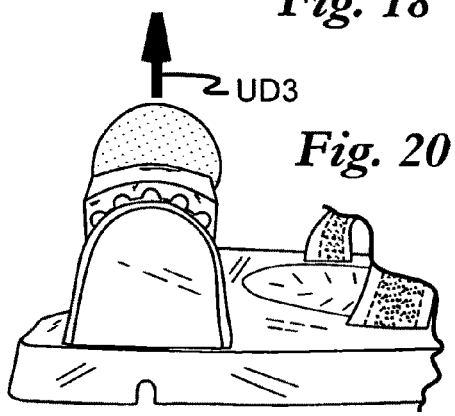
*Fig. 20*
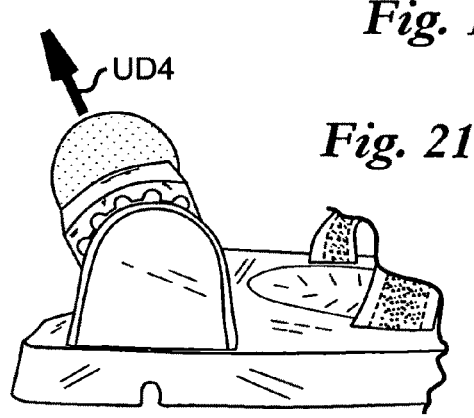
*Fig. 21*

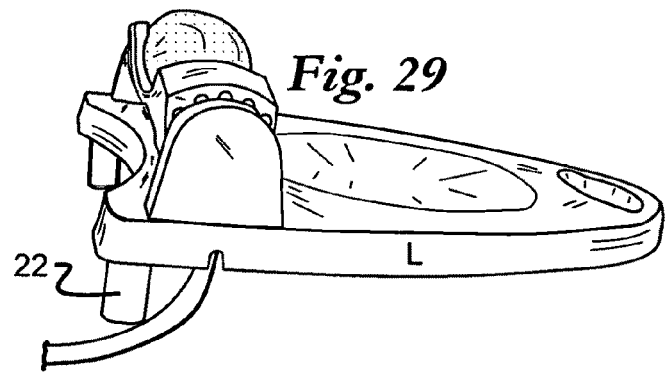
Fig. 29
Fig. 30
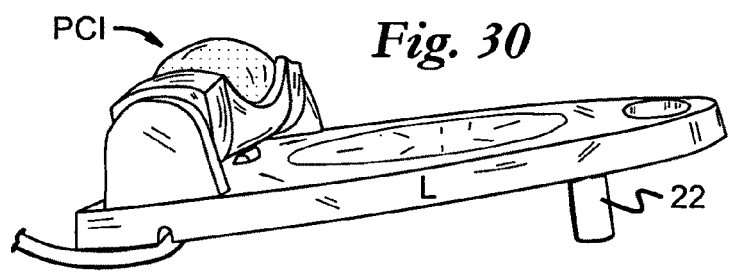
-- Prior Art --
Fig. 31

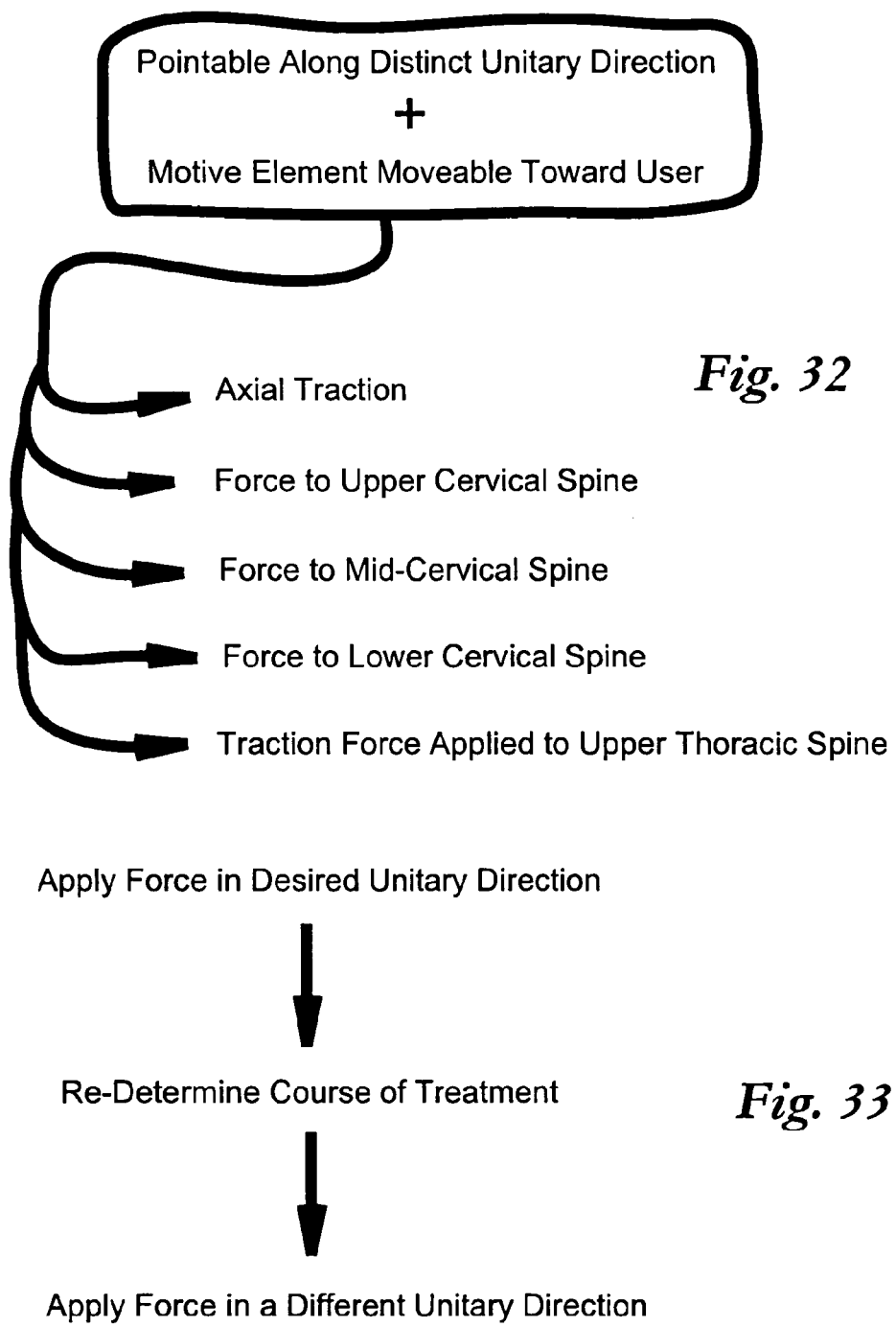

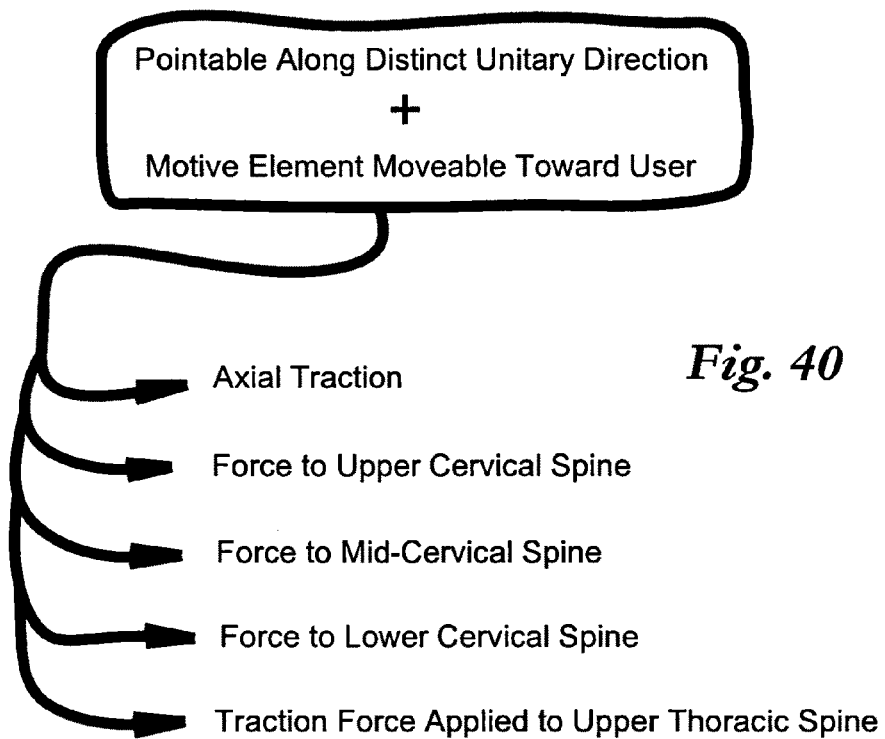
*Fig. 40*
*Fig. 41*

SPINAL TRACTION AND RESTORATION USING POINTABLE CONSTRAINED INFLATOR

CROSS-REFERENCE TO RELATED APPLICATION

This application claims the benefit of U.S. Provisional application Ser. No. 60/999,077, filed Oct. 15, 2007 entitled, "Spinal Traction and Restoration Using Pointable Constrained Inflator," and is hereby incorporated by reference in its entirety.

FIELD of the INVENTION

This invention relates to spinal traction and restoration devices for correction and therapeutic exercise of the human spine. More specifically, it relates to spinal traction and restoration using application of pointable force in distinct directions upon the body, and on the cervical and lumbar spine in particular.

BACKGROUND OF THE INVENTION

The human spine is a main structural support for the body, as well as a conduit for nerve bundles that communicate with the brain. The spine comprises bony masses called vertebra that are linked by flexible tissue, separated by flexible intervertebral discs, and structurally joined by ligaments. A healthy human spine (see the description for FIG. 1 below) possesses curvatures along the sagittal plane: forward leaning curves called lordotic curves in the cervical and lumbar regions, and a rear-leaning curve in the thoracic region called kyphosis. These curvatures are essential for balance, freedom of movement, pain-free living, and healthy circulation of bodily fluids in and around the spine.

Persons with improper, flattened, or reversed lordotic and kyphotic curves, whether due to injury, neglect, or pathology tend to suffer from decreased natural joint movement and also decreased or non-existent fluid transfer around the spinal region, such as decreased circulation throughout the canaliculi or microscopic passages in bone tissue, as well as decreased overall blood circulation. This can be problematic because active transport is needed to prevent degradation of the spinal discs. Also, the mechanical penalty for flat or reversed lordotic curves is that the intervertebral discs also degenerate from the load imposed by the head and during movements like walking and jumping. So when needed, the restoration of healthy lordotic curves, such as by judicious imposition of force therapies, can be extremely important for health and longevity.

Spinal traction and restoration devices have been proven successful in many cases in relieving pain, pressure and inflammation in the cervical and lumbar spine as well as restoring the cervical and lumbar lordosis (forward curve), to great therapeutic benefit. This has been particularly valuable for treatment after injuries and accidents, where a sudden movement of the head or neck, along with whiplash or rebound, causes injury to surrounding and supporting tissues of the neck and head, including injury to the intervertebral joints, discs, ligaments, muscles, nerve roots and blood vessels.

Prior art traction devices have typically used solid neck supports, weights, chin restraining straps and a single, fixed position of tractional force. These devices are said to be uncomfortable, and can cause an undue amount of stress. It is also not possible in the prior art to direct the tractional force specifically to the area of maximum therapeutic effect.

Much of the prior art is devoted to the mechanical imposition of a form (or the equivalent) upon the spine to induce healthy lordosis. U.S. Pat. No. 5,382,226 to Graham discloses an inflatable cervical traction and exercising device which imposes a somewhat spherical form onto the cervical spine in an effort to produce normal lordosis, as discussed below. The device of Graham '226 uses an unconstrained bladder which tends to be non-differentiating, and amounts to merely pushing a spherical body onto the cervical spine. The device of Graham '226 cannot provide true or direct longitudinal traction, or targeted force for therapeutic benefit.

The spinal therapy machine of U.S. Pat. No. 6,652,564 to Harris et al. describes a constraint running around the sides and ends of an inflatable bladder, but the bladder is not capable of producing pointable, direction-selective force, and no specific action on specific vertebra is taught or suggested. Therapeutic actions are taken generally on the cervical and/or lumbar spine, but no specific teaching is given for adjusting significantly the direction of force applied thereon.

SUMMARY OF THE INVENTION

It is an object of the invention to allow a spinal traction and restoration device to cause specific desired forces in a number of distinct unitary directions to be directed to various locations for therapeutic benefit, such as the base of the skull, the cervical spine, and the upper thoracic region. The application of pointable, direction-selective force allows therapies not possible using prior art devices. For example, one can obtain true or direct longitudinal traction when a unit containing a user-selectable pointable constrained inflator is set to the most cephalic position, as described below. When adjusted to other positions, the unit will exert the desired force to the area of the cervical/upper thoracic spine that will afford the user the best results in promoting the restoration of the desired lordotic cervical curve. The use of an inflator or bladder is suggested here in a preferred embodiment, especially as it enhances device comfort and adaptability to patients of differing sizes, weights, ages, and differing tissue pliability and resiliency, However, a pneumatic inflator as shown is not strictly necessary, as discussed below in the description for FIG. 28.

The present invention overcomes shortcomings in the prior art by having the ability to easily adjust the direction of the tractional force to the position of maximum therapeutic benefit. And to great benefit, treatments are can be directed to individual vertebra, or to pairs or groups of adjacent vertebra.

A spinal traction and restoration device is disclosed, allowing pointable application of force to a user who is strapped to, or lying on a device base. The device comprises a motive element so suspended, sized, formed and positioned to be [1] pointable with respect to the device base along a distinct unitary direction, and [2] moveable generally toward the user proximate the device base along that distinct unitary direction.

The motive element can be so formed to be selectively pointable along a plurality of possible distinct unitary directions, which yields freedoms for administering various therapeutic treatments.

The motive element can be fabricated from any number of known materials such as from a metal or plastic form, or preferably can comprise a pointable constrained inflator that is so sized, formed, and positioned so as to move forceably in the desired distinct unitary direction. The pointable constrained inflator can comprise rigid or relatively rigid side walls formed, shaped, sized and positioned as to house an inflatable bladder in a cavity formed therein, wherein the inflatable bladder is so sized, placed, and formed to be constrained upon inflation to move preferentially in the distinct unitary direction, as opposed to merely spherically, like a child's balloon. The pointable constrained inflator can likewise be pointed in a plurality of possible distinct unitary directions, and it can be sized and constrained to have a width (or other dimension applied to the body) equal to a vertebral spacing, two times a vertebral spacing, or three times a vertebral spacing, for precise therapeutic effect.

The invention also comprises a method for restoring a healthy spine using a pointable application of force thereupon. Possible steps include [1] machine forcing the motive element pointed along a distinct unitary direction toward the spine, so as to produce a corresponding line-of-drive force so as to produce preferentially any of: [a] axial traction; [b] force to the upper cervical spine, [c] force to the mid-cervical spine, [d] force to the lower cervical spine, and [e] traction force applied to the upper thoracic spine. One can select the distinct unitary direction from a plurality of distinct unitary directions.

The method can also include additional steps which can customize the therapeutic actions, such as by [3] stopping the machine-forcing and the line-of-drive force; [4] re-determining the course of treatment; and [5] re-applying the original method to produce a different unitary direction (and line of force) than previously obtained.

The preferred embodiment of the invention comprises, as stated, a pointable constrained inflator assembly which can comprise [a] a constrained inflator or bladder so formed and sized to be constrained upon inflation to move preferentially in the distinct unitary direction; and a cradle rotatable with respect to the device base, and in mechanical communication with the constrained inflator, and so sized, formed and positioned, to allow pointing of the constrained inflator in the distinct unitary direction. The cradle can be so formed and sized to surroundingly house the constrained inflator, and be sized as mentioned to correspond with one, two or three times the vertebral spacing.

BRIEF DESCRIPTION OF THE DRAWINGS

FIG. 4 shows a frontal surface view of the spinal restoration device of FIG. 3;

FIG. 5 shows a prior art depiction in cross section of potential inflation directions for the prior art spinal restoration device of FIGS. 2-4;

FIG. 6 shows three time-sequenced cross-sectional inflator profiles for the prior art spinal restoration device of FIGS. 2-4;

FIGS. 15-17 show views similar to those of FIGS. 12-14, showing inflation progression and inflator constraints;

FIGS. 18-22 show partial side views from an oblique perspective of the spinal traction and restoration device according to the invention with the pointable constrained inflator set to provide a pointable application of force by being pointed to five distinct unitary directions;

FIGS. 29 and 30 show oblique side views of the spinal traction and restoration device according to the invention, using legs to elevate one or the other end of the device to provide extension and flexion, respectively;

FIG. 31 shows a schematic description of a prior art method to impose a form on the spine using a bladder inflated to expand in two directions;

FIG. 32 shows a schematic description of two aspects of the spinal traction and restoration device according to the invention which provide for distinct forces as indicated;

FIG. 33 shows a schematic description of a method according to the invention.

DEFINITIONS

The following definitions shall be used throughout:

Constrained/constraint—in the context of an inflator shall denote boundary conditions which prevent substantial expansion or movement in an direction other than a distinct unitary direction. The boundary conditions can be, but do not have to be the result of constraining a bladder or other fluid filled body, and can be the result of design which favors an inflation direction over other directions, or which only allows significant motion in the distinct unitary direction. For this purpose, a conventional air-filled bladder can be supplemented with a wire form or other structural element that provides needed constrained behavior.

Device base—shall denote any material body or surface which defines generally a platform for supporting a person or patient. It shall also include any generally planar surface that is merely adjacent a user or patient, such as a device board which is oriented vertically for a standing patient.

Inflator—shall include any and all constraints and moveable housings, cradles and indexing hardware, such as provided by the pointable constrained inflator as given here illustratively. An inflator need not be pneumatic or make use of an inflatable (e.g., air) bladder, and can be an electrically operated (e.g., magnetic solenoid operated) device that causes a motive surface to protrude.

Line of Drive—shall denote a resultant force, with a magnitude and a direction, impressed upon the body of a user through use of the instant invention.

Pneumatic—shall include reference to any and all fluids, including liquids, gases, powders or other material bodies that can provide inflation of an inflator when desired.

Point/Pointed/Pointable—shall include any equivalent action, including having tiltable constraint walls that produce different distinct unitary directions.

Pointable constrained inflator—shall denote a force producing device that utilizes a constrained inflator which produces force in a distinct unitary direction that can be changeable to any one of a plurality of distinct unitary directions.

DETAILED DESCRIPTION

Figure 1:
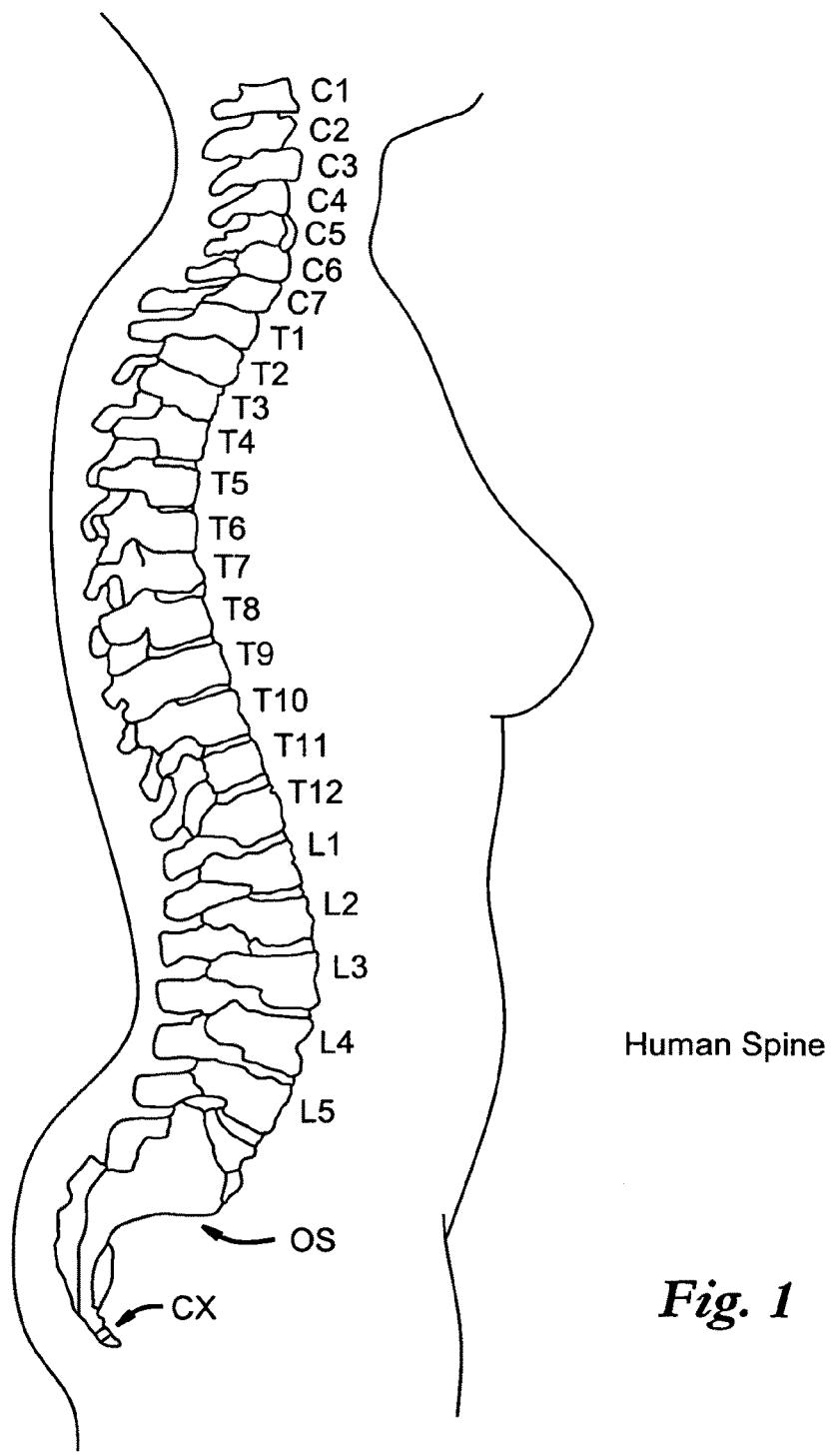
FIG. 1 shows a cross-section of a healthy human spine, showing cervical, thoracic and lumbar vertebra.

Now referring to FIG. 1, a cross-section of a representative healthy human spine with forward lordosis of the cervical and lumbar regions, and showing cervical, thoracic and lumbar vertebra, numbered as shown (C1-C7, T1-T12, and L1-L5, respectively), as well as os sacrum OS and coccyx Cx. Many therapeutic treatments are specific to these separate spinal regions. As mentioned above, the normal or healthy human spine exhibits certain characteristics, including what known lordotic curves (lordosis), a forward curve found in the cervical and lumbar regions, and as shown in the figure. There is a large body of knowledge developed concerning the spine and surrounding tissue (Reference: Principles and Practices of Chiropractic, Scott Haldeman, McGraw-Hill Medical; 3 edition (Mar. 1, 2004), ISBN-10: 0071375341 and ISBN-13: 978-0071375344), which is herein incorporated in its entirety.

Figure 2:
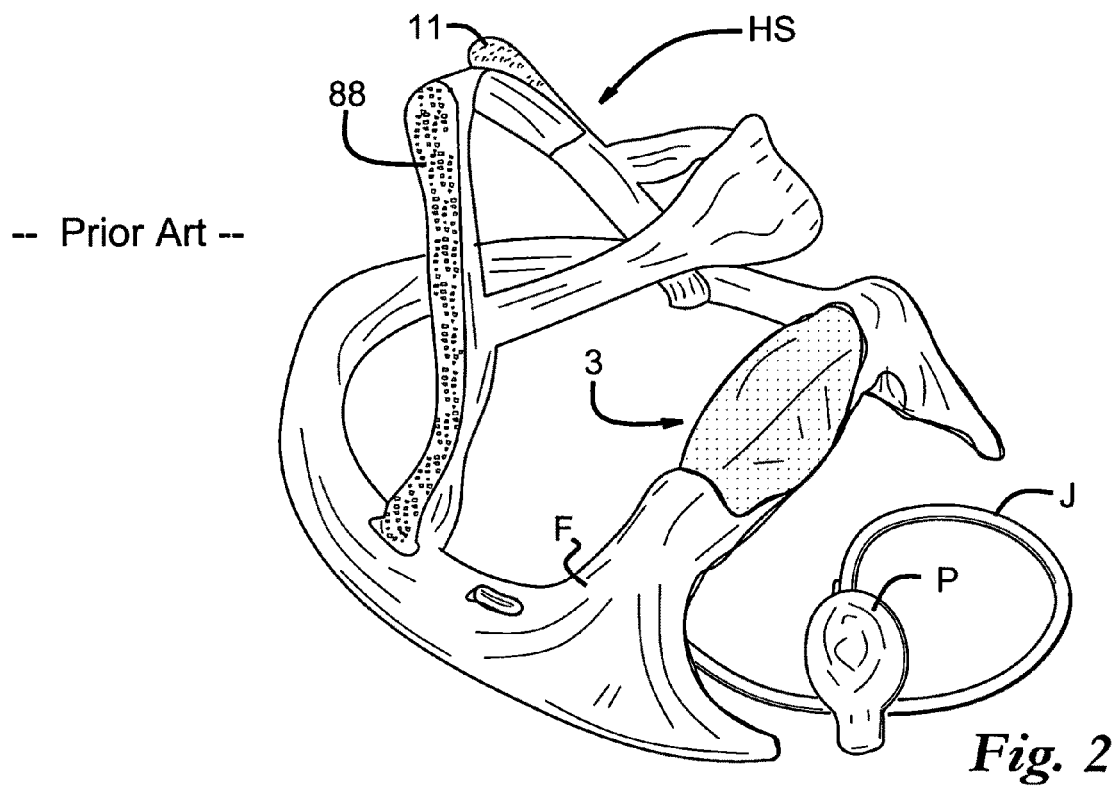
FIG. 2 shows and oblique surface view of a prior art spinal restoration device.

Now referring to FIG. 2, an oblique surface view of a prior art spinal restoration device is shown. Like many such devices, a user rests on a device, placing the head and neck onto a base assembly which includes elements for applying force for traction and restoration of proper form, including lordotic curves. This prior art spinal restoration device comprises an inflatable bladder 3 housed in a frame F. The bladder 3 is fillable in a known manner using an inflation bulb P connected to an air hose J as shown. A user can optionally strap the head to the frame F using head strap HS and Velcro® strips 88 and 11. To impose force, the neck of a user is contacted by inflatable bladder 3. Upon inflation, bladder 3 bears upon the neck. However, the resultant force produced by an unconstrained bladder is not precisely delivered and cannot be delivered in a distinct unitary direction.

Figure 3:
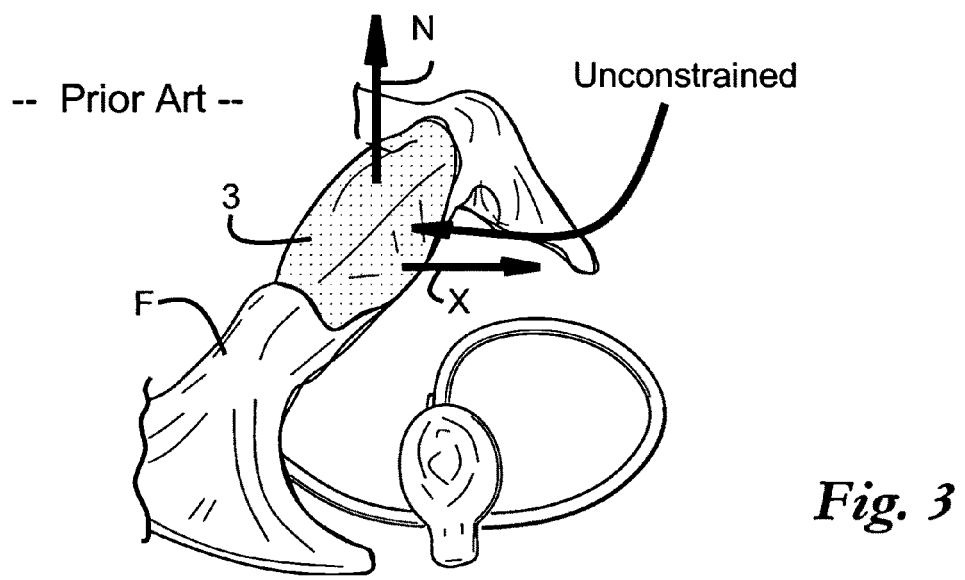
FIG. 3 shows a partial view of the prior art spinal restoration device of FIG. 2, showing potential inflation directions and an unconstrained inflator.

Referring to FIG. 3, a partial view of the prior art spinal restoration device of FIG. 2 is again given, showing potential mutually perpendicular inflation directions (normal) N and (transverse) X for the bladder or unconstrained inflator 3. These inflation or expansion directions N and X are essentially produced on a par with respect to each other, and produce the inflation profile as described below in FIG. 6.

An added illustration is given by FIG. 4, which shows a frontal surface view of the same spinal restoration device of FIG. 3, and reveals that the inflatable bladder 3 is unconstrained by frame F (shown, Unconstrained).

To show the result obtained by using an unconstrained inflator, FIG. 5 shows a prior art depiction in cross section of potential inflation directions for the prior art spinal restoration device of FIGS. 2-4, and as shown, inflatable bladder 3 inflates along the directions shown by arrows and represents merely a spherical form which is imposed upon the cervical spine as shown. Such an imposition of a spherical or nearly spherical form is taught in the prior art. It yields a force applied over many vertebra, with no action specific to a single vertebra, and no true directional force application possible.

To illustrate further, FIG. 6 shows three illustrative time-sequenced cross-sectional inflator profiles for the prior art spinal restoration device of FIGS. 2-4. Three inflator profiles C1-C3 are shown, with moving centers shown by very small interior circles. As the inflator expands, the effective center of the inflator does not move substantially upward, as shown by the minimal departure of the profiles C2 and C3 from the center line CL of the first profile C1.

Figure 7:
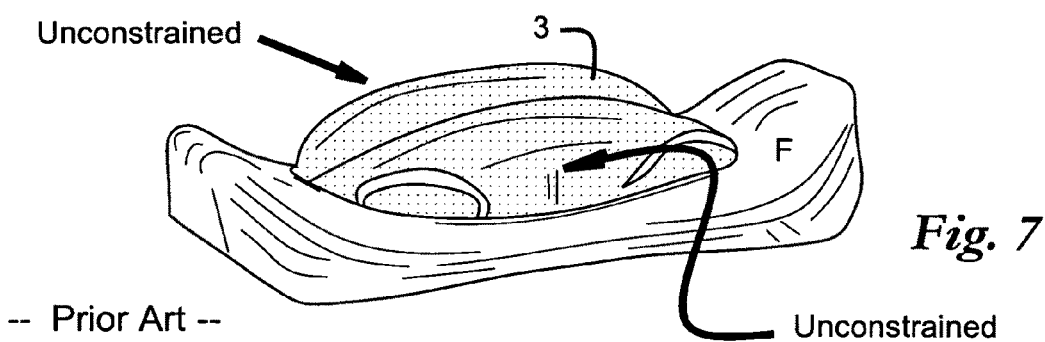
FIG. 7 shows an oblique surface view of another prior art spinal treatment device, showing an unconstrained inflator.

FIG. 7 shows an oblique surface view of another prior art spinal treatment device, showing another unconstrained inflator 3 held inside a frame F. As can be seen from the figure, the unconstrained inflator 3 is not supported or constrained, for example, on the sides (shown, Unconstrained). Upon inflation, this results in an imprecise, somewhat circular inflation profile as illustratively shown in FIG. 6. This is a further illustration of a prior art device using an unconstrained inflator.

Figure 8:
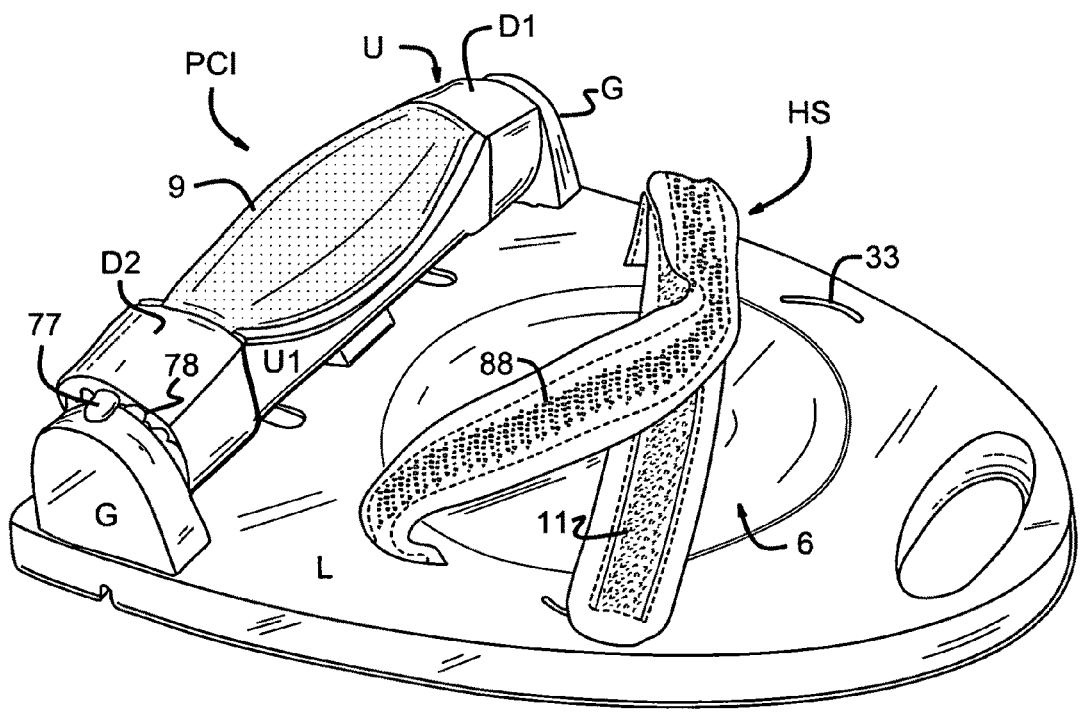
FIG. 8 shows an oblique surface view of a spinal traction and restoration device according to the invention.

FIG. 8 shows an oblique surface view of a spinal traction and restoration device according to the invention. Device base L accommodates optional head strap HS, which comprises two straps self affixable using Velcro® strips 88 and 11, allowing positioning of a user's head inside scallop or depression 6, with the user's neck resting upon a inflatable bladder 9, which is part of a pointable constrained inflator PCI as shown to the left in the figure. Pointable constrained inflator PCI comprises support arms G which support a cradle U. Cradle U comprises end caps D1 and D2 which house an indexing mechanism 77 as shown, which allows cradle U to rotate and stop in various positions, as further shown below. Indexing mechanism 77 mechanically communicates with index slots 78 formed in end cap D2. End caps D1 and D2 support cradle side walls U1, which are so sized positioned and formed as to constrain and retain inflatable bladder 9 as shown in the uninflated state.

Figure 9:
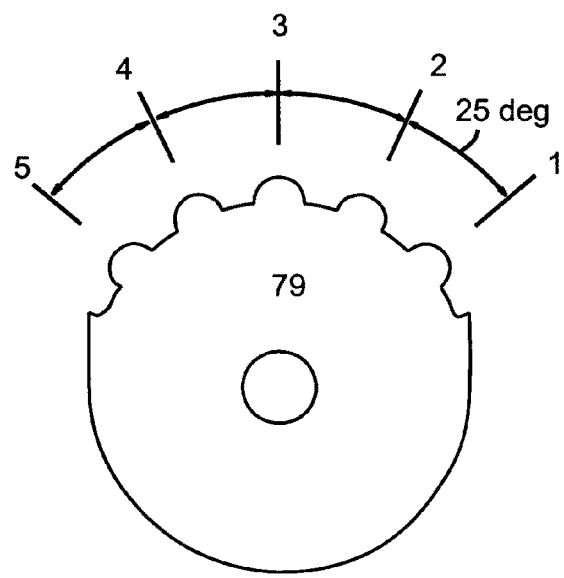
FIG. 9 shows a cross-sectional view of an indexing plate used by the spinal traction and restoration device shown in FIG. 8.

To further illustrate the indexing mechanism 77, FIG. 9 shows a cross-sectional view of an indexing plate 79 used by indexing mechanism 77 to effect increments of angle for cradle U, with five 25-degree increments illustratively shown. The indexing mechanism can be formed by those skilled in the mechanical arts to exhibit differing numbers and sizes of angular increments without departing from the scope of the invention.

Figure 10:
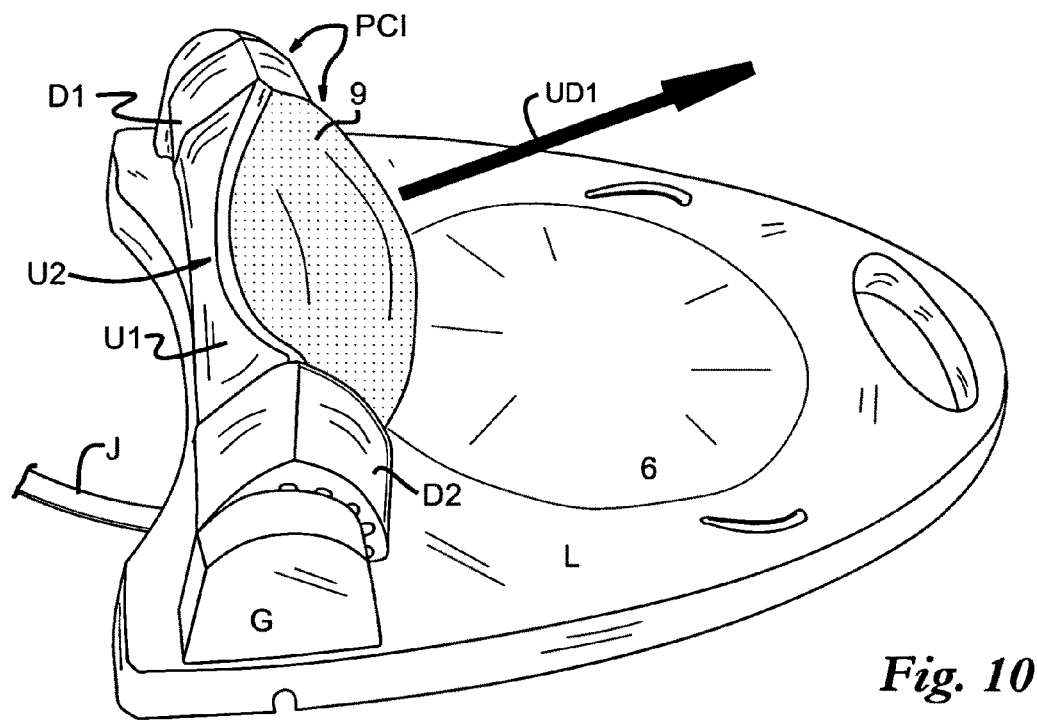
FIG. 10 shows the spinal traction and restoration device of FIG. 8, with a pointable constrained inflator cradle rotated to provide an application of force along an extreme unitary direction.

Now referring to FIG. 10, the spinal traction and restoration device of FIG. 8 is shown, with the pointable constrained inflator cradle rotated to an extreme rightward or cephalic position as shown to provide an application of force along an extreme unitary direction UD1. Cradle side walls U1 can comprise a cradle cutout for user comfort U2 which is nonetheless so sized and positioned so as not to interfere with needed constraints provided by cradle side walls U1. With inflatable bladder 9 so constrained, it acts as a narrow motive element to great therapeutic advantage. It is preferably sized to have the magnitude of at least one dimension thereof to be within 3 times the size of a vertebral spacing for said user. Inflatable bladder 9 as exposed is approximately 15 cm long and 3-4 cm wide.

Though not shown, cradle side walls U1 can be tiltable, using known mechanical arts, so as to further constrain the inflatable bladder 9 on demand.

Figure 11:
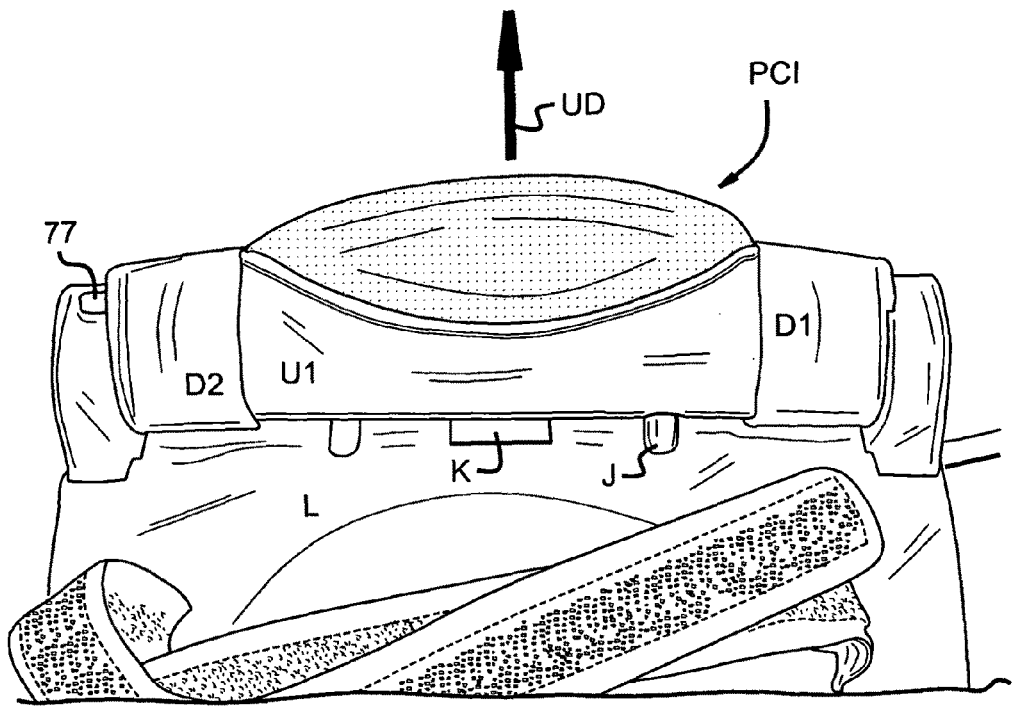
FIG. 11 shows the spinal traction and restoration device of FIG. 8 with a frontal view of the pointable constrained inflator cradle.

FIG. 11 shows the spinal traction and restoration device of FIG. 8 with a partial frontal view of the pointable constrained inflator cradle U1 shown in a somewhat inflated state, providing a top surface as shown in the figure which moves generally toward the user in distinct unitary direction UD as shown. Optional support K can help cradle side walls U1 from bowing downward under user pressure.

Figures 12, 13, 14:
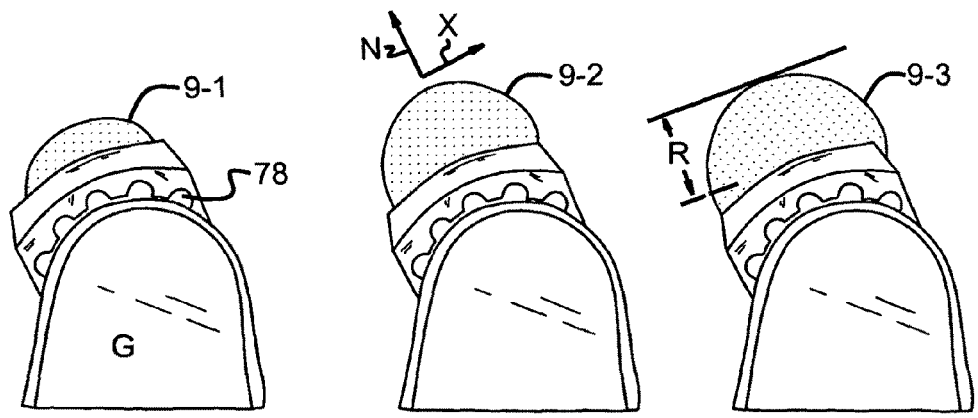
FIGS. 12-14 show three time-sequenced side views of a pointable constrained inflator according to the invention, giving part-surface views, and part cross-sectional views during inflator inflation.
Figure 22:
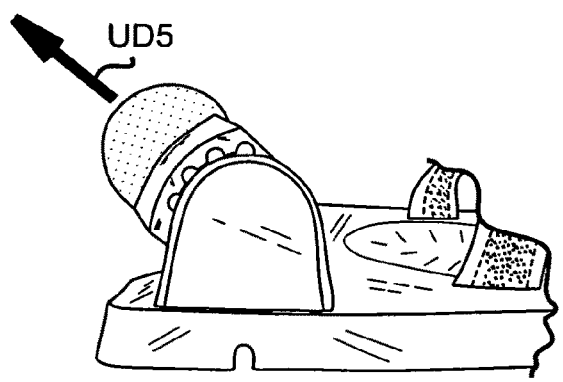

To show illustrative inflation profiles using the pointable constrained inflator of the invention, FIGS. 12-14 show three time-sequenced side views of a pointable constrained inflator, giving part-surface views, and part cross-sectional views during inflator inflation. As inflatable bladder 9 fills, the profile changes from those shown, 9-1 to 9-2 to 9-3, moving generally outward a distance R as shown, with most movement in a distinct unitary direction shown in the figure as N. This is in contrast with the inflation profile illustrated in FIG. 6. The constraint provided by cradle side walls U1 provides an inflation profile that is useful in that it protrudes, as the effective center of the inflated bladder moves away from the cradle. The inflator profile is sized preferably to be on the same order as the vertebral spacing of the user.

FIG. 15 shows a view similar to that of FIGS. 12-14, but giving the same progressive inflator profiles 9-1, 9-2, and 9-3 shown superimposed upon one another for comparison. As shown in FIG. 16, an inside cutout CO of the cradle reveals an air filled bladder (shown, A) housed inside a cavity Y as shown, which forces it upon inflation to assume the shape shown. An alternate folded bladder configuration is shown in FIG. 17, where bladder ends 9A and 9B are affixed as known in the art using fasteners or glue (not shown) to cradle side walls U1. Those skilled in the art can vary the bladder schemes or configurations to advantage without departing from the scope of the invention such as by using a tucked or folded bladder (not shown) to achieve possible design objectives such as low cost or longevity. A folded bladder can work cooperatively with cradle side walls U1 to provide the necessary constraint and application of force in a distinct unitary direction.

Figure 23:
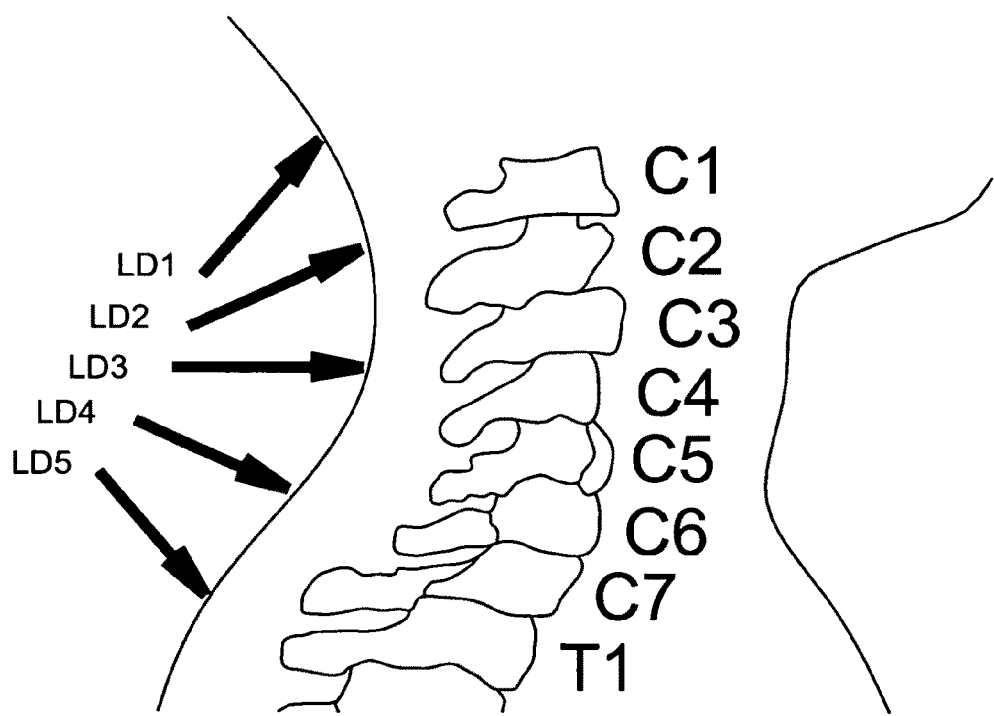
FIGS. 23 and 24 show close-up partial views of the human spine shown in FIG. 1, each showing five distinct potential lines of drive for the application of force using the spinal traction and restoration device according to the invention.
Figure 24:
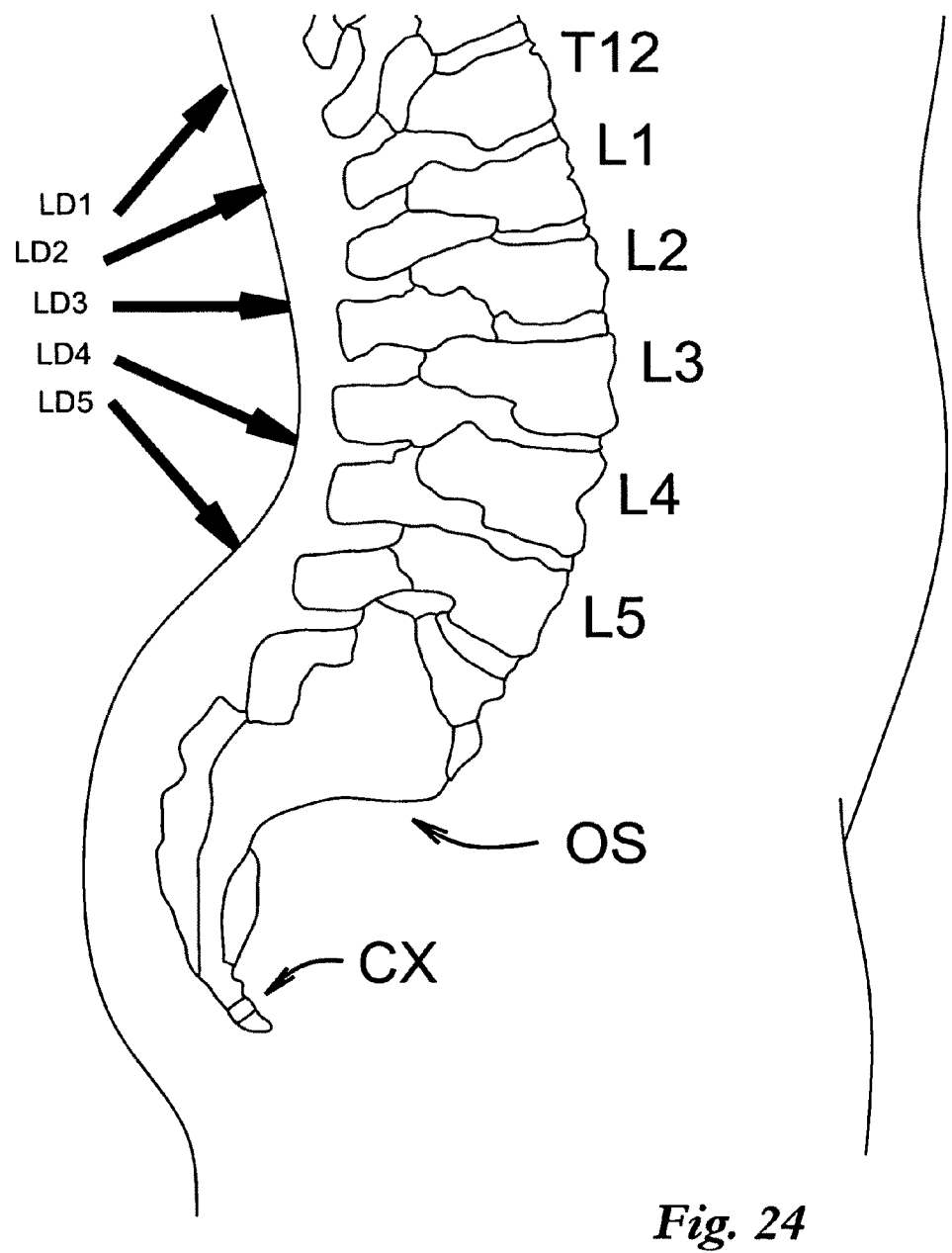

To further illustrate the application of force along a plurality of possible distinct unitary directions using the invention, refer to FIGS. 18-22, which show partial side views from an oblique perspective of the spinal traction and restoration device. As shown in the figures, the pointable constrained inflator is set using the indexing mechanism previously described to provide a pointable application of force by being pointed to five distinct unitary directions UD1-UD5 as shown, approximately 25 rotational degrees apart. This can, for example, allow the cervical line-of-drive forces LD1-LD5 as shown in FIG. 23 and similar forces to the lumbar spine as shown in FIG. 24.

Figure 25:
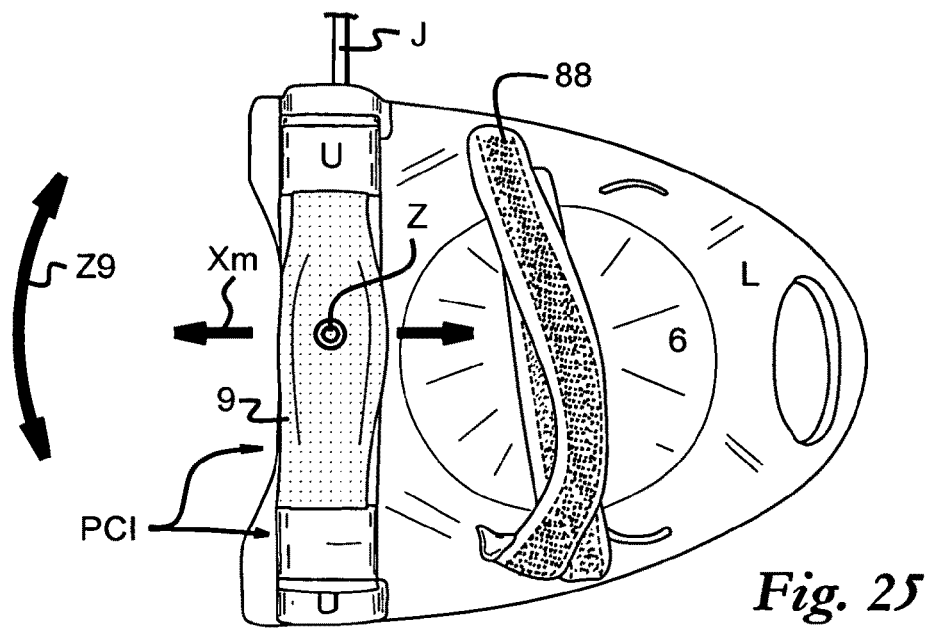
FIGS. 25 and 26 show top views of the spinal traction and restoration device according to the invention, additionally showing possible translation and/or rotation of the pointable constrained inflator with respect to a device base.
Figure 26:
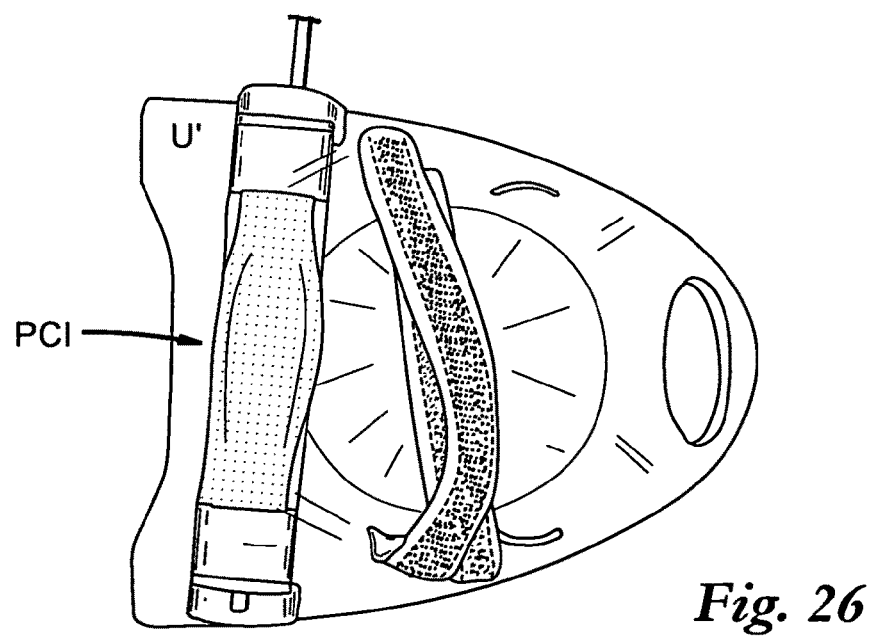

It is possible, for greater therapeutic application, to use known mechanical principles to modify the angle that the cradle U makes on the device base L. It is also possible to change the location of the cradle U with respect to the base and the depression 6 for the head. FIG. 25 shows a top view of the spinal traction and restoration device according to the invention, additionally showing possible translation Xm and/or rotation Z9 about vertical axis Z (out of the page) as shown of the pointable constrained inflator with respect to a device base L. FIG. 26 shows an angular change of the orientation of the cradle U on the device base L. Such changes can be beneficial to accommodate patients of different sizes, and for different pathological conditions.

Figure 27:
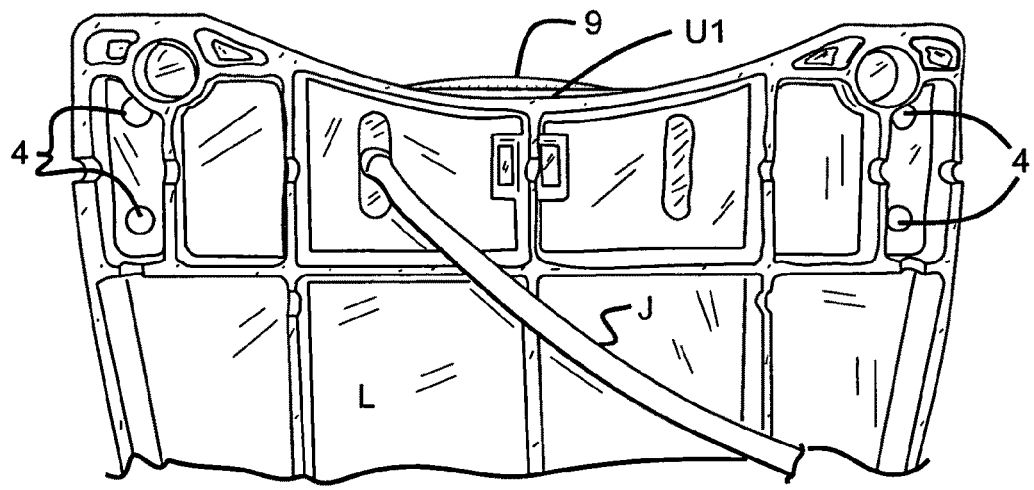
FIG. 27 shows an underside of a device base of the spinal traction and restoration device according to the invention, with potential fastening points for the pointable constrained inflator.

To further illustrate, FIG. 27 shows an underside of a device base of the spinal traction and restoration device according to the invention, with potential fastening points 4 for the pointable constrained inflator. By moving fastening points 4, the rotation and/or translation of the pointable constrained inflator can be effected. Alternatively, in lieu of moving fastening points 4, a machine actuable arrangement known in the art can be used to move the pointable constrained inflator automatically or upon demand.

Figure 28:
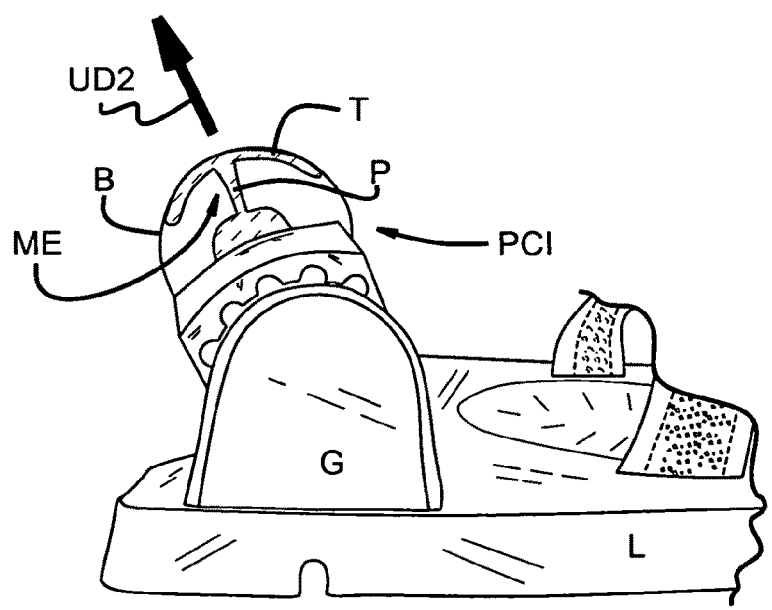
FIG. 28 shows a partial side view from an oblique perspective similar to that of FIGS. 18-22, where the inflator of the pointable constrained inflator has been replaced by a motive element provide equivalent function.
Figure 34:
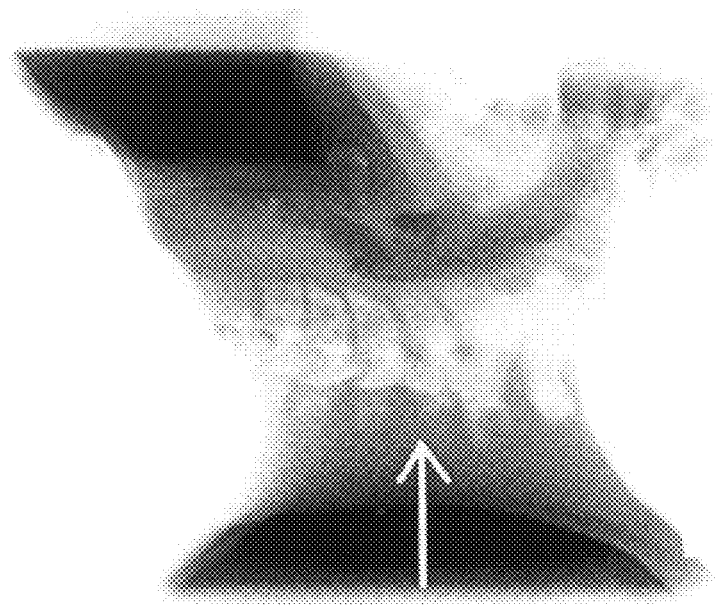
Figure 35:
Figure 36:
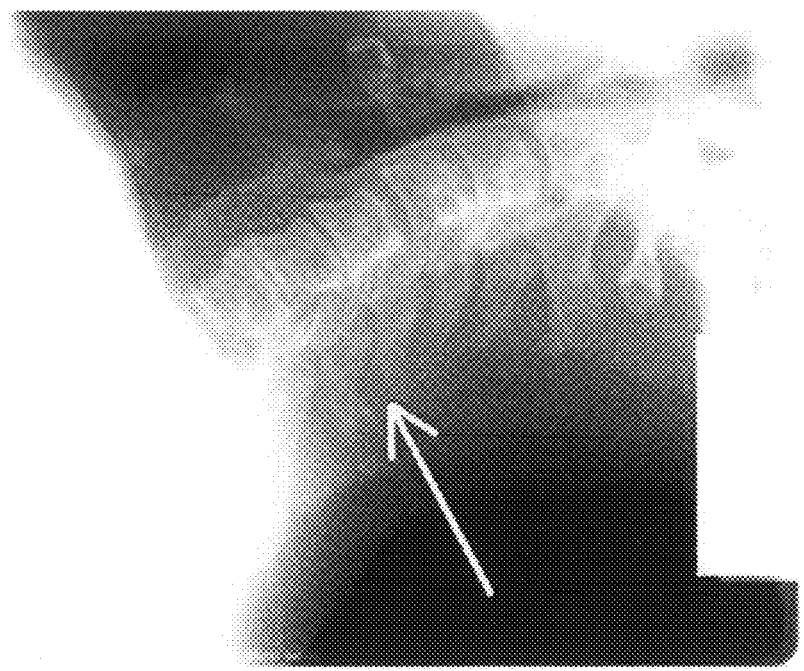
Figure 37:
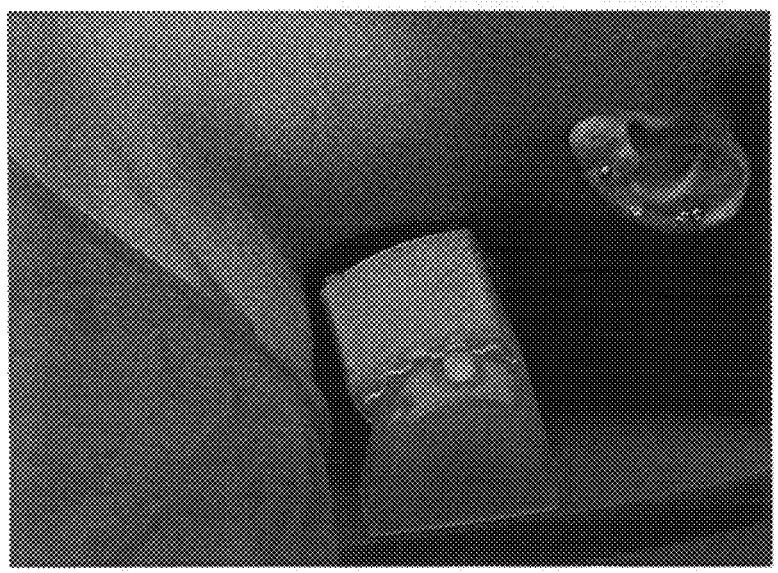
Figure 38:
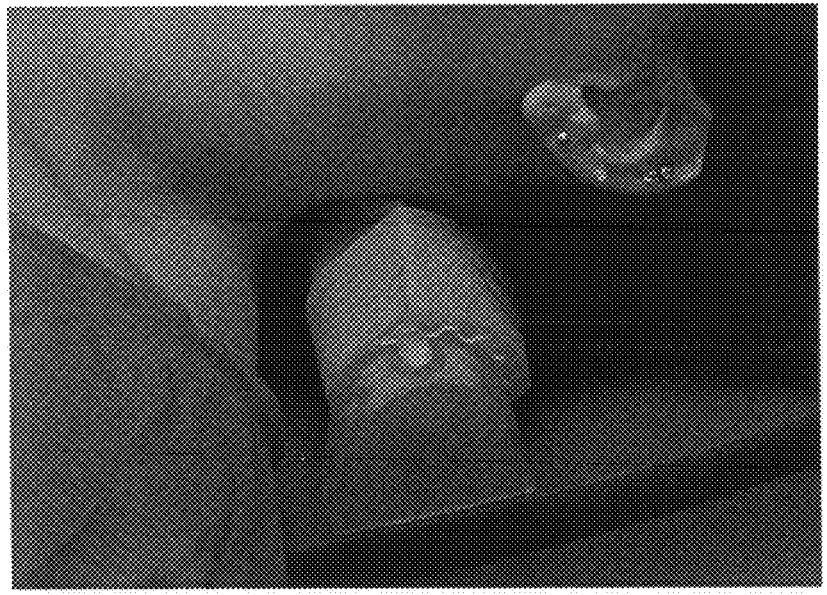
Figure 39:
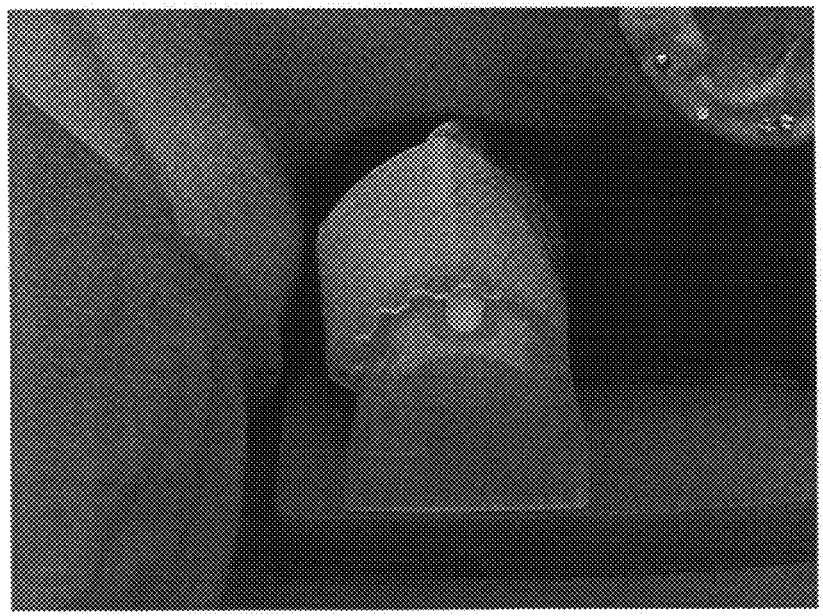

Generally, the pointable constrained inflator can be replaced by a motive element performing a similar function. Referring now to FIG. 28, a partial side view from an oblique perspective similar to that of FIGS. 18-22 is shown, where the inflator of the pointable constrained inflator has been replaced by a motive element ME which provides an equivalent function. Motive element ME can comprise as shown a contactor T and a push rod P as shown, which act to move boot B as shown. Boot B can be a membrane, or can be a form, such as a plastic form. Push rod P can be moveable using known servo motors or actuators, and can be controlled using known robotics. Such a machine actuable device can be moved by a solenoid, or other electro-mechanical or electropneumatic device (not shown), and subject to controls (not shown). This provides functionality without using a manual pump or inflator, and can allow complex control, remote control, or memory control where a specific force application regimen is reproduced for the benefit of a patient.

In a similar vein, the tilt of the device base L can be changed. Referring to FIGS. 29 and 30, oblique side views of the spinal traction and restoration device according to the invention are shown, One can elevate one or the other end of the device base L to provide extension and flexion, respectively by use of elevating legs or pegs 22 as shown. The legs 22 can be insertable on demand, or can be electrically driven on demand to provide the base tilt desired by the practitioner or patient.

FIG. 31 shows a schematic description of a prior art method to impose a form on the spine using a bladder inflated to expand in two directions. As shown, a first step, Bladder Inflated to Expand in Two Directions (Spherically) refers to the inflation progression shown in FIG. 5. This allows that one can Impart Desired Lordotic Shape via Imposition of a Form, as shown, which cannot achieve pointable force as taught here.

To illustrate the invention schematically, FIG. 32 shows a schematic description of two aspects of the spinal traction and restoration device according to the invention which provide for distinct forces as indicated. Specifically, with a motive element pointable along a distinct unitary direction, and moveable generally toward a user (shown), any of the following force application modes are now made possible: [1] Axial Traction; [2] Force to Upper Cervical Spine; [3] Force to Mid-Cervical Spine; [4] Force to Lower Cervical Spine; and [5] Traction Force Applied to Upper Thoracic Spine. This makes many specific various therapies possible, using applied forces selected from a plurality of distinct unitary directions.

FIG. 33 shows a schematic description of a method according to the invention, where one applies a force in a desired distinct unitary direction, then re-determines the course of treatment, and then applies forces in a different distinct unitary direction (text shown). This type of versatile treatment is not possible using devices of the prior art.

There is obviously much freedom to exercise the elements or steps of the invention.

The description is given here to enable those of ordinary skill in the art to practice the invention. Many configurations are possible using the instant teachings, and the configurations and arrangements given here are only illustrative.

Those with ordinary skill in the art will, based on these teachings, be able to modify the invention as shown, or apply in ways not explicitly shown here, such as using the pointable constrained inflator to apply directed force to different areas of the body other than the cervical and lumbar spine.

The invention as disclosed using the above examples may be practiced using only some of the features mentioned above. Also, nothing as taught and claimed here shall preclude addition of other structures or functional elements.

Obviously, many modifications and variations of the present invention are possible in light of the above teaching. It is therefore to be understood that, within the scope of the appended claims, the invention may be practiced otherwise than as specifically described or suggested here.

I claim:

1. A spinal traction and restoration device allowing pointable application of force (LD1-LD5) to a user proximate a device base (L), said device comprising:
   a pointable constrained inflator (PCI) having an inflatable bladder (9), said inflatable bladder being so suspended, sized, formed and positioned to be
   [1] pointable with respect to said device base along a distinct unitary direction (UD1, UD2, UD3, UD4, or UD5); and
   [2] moveable generally toward said user proximate said device base along said distinct unitary direction; and
   a cradle defining a cavity (Y) housing and constraining said inflatable bladder of said pointable constrained inflator, said cradle including end caps for constraining lateral ends of said inflatable bladder of said pointable constrained inflator, a bottom wall for constraining the underside of said inflatable bladder of said pointable constrained inflator and two opposed sidewalls (U1) for constraining longitudinal sides of said inflatable bladder of said pointable constrained inflator such that substantially only a top portion of said inflatable bladder is unconstrained and extends toward said user in said distinct unitary direction upon inflation of said inflatable bladder.

2. The spinal traction and restoration device of claim 1, wherein said pointable constrained inflator is so formed to be selectively pointable along said distinct unitary direction selected from a plurality of possible distinct unitary directions (UD1-UD5).

3. The spinal traction and restoration device of claim 2, wherein said pointable constrained inflator (PCI) is so sized, formed and positioned so as to move forceably in said distinct unitary direction selected from said plurality of possible distinct unitary directions.

4. The spinal traction and restoration device of claim 1, wherein:
   said base defines a generally horizontal plane; and
   wherein said cradle is rotatable about an axis generally perpendicular to said horizontal plane defined by said base.

5. A method for restoring a healthy spine using a pointable application of force thereupon, said method comprising:
   providing a pointable constrained inflator (PCI) having an inflatable bladder (9);
   constraining said inflatable bladder on a bottom side, lateral ends and longitudinal sides thereof;
   pointing said pointable constrained inflator along a distinct unitary direction (UD1, UD2, UD3, UD4, UD5) toward said spine; and
   inflating said inflatable bladder such that substantially only an unconstrained top portion of said inflatable bladder extends toward said spine of a user in said distinct unitary direction so as to produce a corresponding line-of-drive force (LD1, LD2, LD3, LD4, LD5) so as to produce preferentially any of: [a] axial traction; [b] force to the upper cervical spine, [c] force to the mid-cervical spine, [d] force to the lower cervical spine, and [e] traction force applied to the upper thoracic spine.

6. The method for restoring a healthy spine using a pointable application of force thereupon of claim 5, said method further comprising selecting said distinct unitary direction from a plurality of distinct unitary directions.

7. The method of claim 5, further comprising;
   deflating said inflatable bladder to stop said line-of-drive force;
   re-determining the course of treatment; and
   re-applying said pointing and said inflating steps to produce a different unitary direction than previously obtained.

8. The method for restoring a healthy spine using a pointable application of force thereupon of claim 5, wherein:
   said pointable constrained inflator is mounted on a base defining a generally horizontal plane, said method further comprising the step of rotating said pointable constrained inflator about an axis generally perpendicular to said horizontal plane defined by said base.

9. A pointable constrained inflator (PCI) for use in a spinal traction and restoration device allowing pointable application of force (LD1-LD5) to a user proximate a device base (L), said pointable constrained inflator comprising:
   [a] a constrained inflator (9) so formed and sized to be constrained upon inflation to move preferentially in a distinct unitary direction (UD1, UD2, UD3, UD4, UD5;
   [b] a cradle (U) rotatable with respect to said device base, and housing said constrained inflator, and so sized, formed and positioned, to allow pointing of said constrained inflator in said distinct unitary direction;
   wherein said base defines a generally horizontal plane; and
   wherein said cradle is rotatable about an axis generally perpendicular to said horizontal plane defined by said base.

10. The pointable constrained inflator of claim 9, wherein said rotatable cradle is so formed and sized to surroundingly house said constrained inflator.

11. The pointable constrained inflator of claim 9, wherein said rotatable cradle is so formed to be indexed to allow a selected fixed distinct unitary direction selected from a plurality of distinct unitary directions.

* * * * *